(12) United States Patent
Kampa

(10) Patent No.: US 7,419,486 B2
(45) Date of Patent: Sep. 2, 2008

(54) TREATMENT AND DIAGNOSTIC CATHETERS WITH HYDROGEL ELECTRODES

(75) Inventor: Gregory J. Kampa, Blaine, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 421 days.

(21) Appl. No.: 11/154,104

(22) Filed: Jun. 15, 2005

(65) Prior Publication Data

US 2007/0005052 A1 Jan. 4, 2007

(51) Int. Cl.
*A61B 18/14* (2006.01)

(52) U.S. Cl. .......................................... 606/32; 606/41

(58) Field of Classification Search .................... 606/32, 606/41
See application file for complete search history.

(56) References Cited

U.S. PATENT DOCUMENTS

| | | | |
|---|---|---|---|
| 4,945,912 A | 8/1990 | Langberg | |
| 5,281,213 A | 1/1994 | Milder et al. .................. | 606/15 |
| 5,281,217 A | 1/1994 | Edwards et al. ............... | 606/41 |
| 5,334,193 A | 8/1994 | Nardella ....................... | 606/41 |
| 5,370,644 A | 12/1994 | Langberg | |
| 5,403,295 A * | 4/1995 | Byrne ......................... | 604/265 |
| 5,431,649 A | 7/1995 | Mulier et al. ................. | 606/41 |
| 5,433,708 A | 7/1995 | Nichols et al. ............... | 604/113 |
| 5,542,928 A | 8/1996 | Evans et al. .................. | 604/113 |
| 5,584,872 A | 12/1996 | LaFontaine et al. .......... | 607/116 |
| 5,609,151 A | 3/1997 | Mulier et al. ................ | 128/642 |
| 5,622,168 A | 4/1997 | Keusch | |
| 5,658,278 A | 8/1997 | Imran et al. .................... | 606/41 |
| 5,676,693 A | 10/1997 | LaFontaine ................. | 607/116 |
| 5,697,927 A | 12/1997 | Imran et al. .................... | 606/41 |
| 5,725,524 A | 3/1998 | Mulier et al. ................. | 606/41 |
| 5,785,706 A | 7/1998 | Bednarek ..................... | 606/41 |
| 5,807,306 A | 9/1998 | Shapland | |
| 5,876,398 A | 3/1999 | Mulier et al. ................. | 606/41 |
| 5,895,417 A | 4/1999 | Pomeranz et al. ........... | 607/101 |
| 5,913,854 A | 6/1999 | Maguire et al. .............. | 606/41 |
| 5,913,856 A | 6/1999 | Chia et al. .................... | 606/41 |
| 5,919,188 A | 7/1999 | Shearon et al. .............. | 606/41 |

(Continued)

OTHER PUBLICATIONS

PCT International Search Report and Written Opinion of the International Searching Authority for PCT/US06/23305, dated Jul. 20, 2007, 10 pages.

*Primary Examiner*—Lee S Cohen
(74) *Attorney, Agent, or Firm*—Heimbecher & Assoc., LLC

(57) ABSTRACT

Straight and curved catheters for treatment or diagnoses of tissue, including cardiac tissue, using hydrogel virtual electrodes and hydrogel sensing electrodes are disclosed. Each catheter comprises at least one conductive hydrogel electrode, whether a virtual electrode or a sensing electrode. Hydrogel virtual electrodes may be used to deliver ablative energy or chemotherapeutic agents to tissue. Hydrogel sensing electrodes may be used to map various electrical activity of tissue. The ablation catheters include a variety of hydrogel delivery features to deliver the conductive hydrogel electrodes against or adjacent to tissue to be treated. Each hydrogel delivery feature comprises at least one opening in the distal portion of the catheter and may also include a permeable or semi-permeable membrane. The mapping catheters include conductive hydrogel disks (i.e., conductive hydrogel sensing electrodes) and nonconductive hydrogel disks. Methods of treating and diagnosing tissue using hydrogel virtual electrodes and hydrogel sensing electrodes are also disclosed.

25 Claims, 11 Drawing Sheets

U.S. PATENT DOCUMENTS

| | | | |
|---|---|---|---|
| 5,971,968 A | 10/1999 | Tu et al. | 604/264 |
| 5,997,532 A | 12/1999 | McLaughlin et al. | 606/41 |
| 6,010,500 A | 1/2000 | Sherman et al. | 606/41 |
| 6,015,407 A | 1/2000 | Rieb et al. | 606/41 |
| 6,016,809 A | 1/2000 | Mulier et al. | 128/898 |
| 6,032,077 A | 2/2000 | Pomeranz | 607/101 |
| 6,063,080 A | 5/2000 | Nelson et al. | 606/41 |
| 6,068,653 A | 5/2000 | LaFontaine | 607/116 |
| 6,080,151 A | 6/2000 | Swartz et al. | 606/45 |
| 6,119,041 A | 9/2000 | Pomeranz et al. | 607/101 |
| 6,120,476 A | 9/2000 | Fung et al. | 604/95 |
| 6,120,500 A | 9/2000 | Bednarek et al. | 606/41 |
| 6,132,426 A | 10/2000 | Kroll | 606/41 |
| 6,168,594 B1 | 1/2001 | LaFontaine et al. | 606/41 |
| 6,171,275 B1 | 1/2001 | Webster, Jr. | 604/20 |
| 6,217,576 B1 | 4/2001 | Tu et al. | 606/41 |
| 6,219,582 B1 | 4/2001 | Hofstad et al. | 607/122 |
| 6,235,022 B1 | 5/2001 | Hallock et al. | 606/41 |
| 6,235,044 B1 | 5/2001 | Root et al. | 606/200 |
| 6,238,393 B1 | 5/2001 | Mulier et al. | 606/41 |
| 6,241,722 B1 | 6/2001 | Dobak et al. | 606/23 |
| 6,409,722 B1 | 6/2002 | Hoey et al. | 606/34 |
| 6,454,766 B1 | 9/2002 | Swanson et al. | 606/41 |
| 6,464,699 B1 * | 10/2002 | Swanson | 606/41 |
| 6,605,087 B2 | 8/2003 | Swartz et al. | 606/41 |
| 6,640,118 B2 * | 10/2003 | Van Heerden et al. | 600/372 |
| 6,671,561 B1 * | 12/2003 | Moaddeb | 607/120 |
| 6,702,811 B2 | 3/2004 | Stewart et al. | |
| 6,858,026 B2 | 2/2005 | Sliwa et al. | 606/28 |
| 6,984,232 B2 * | 1/2006 | Vanney et al. | 606/41 |
| 2002/0099277 A1 | 7/2002 | Harry | |
| 2004/0059327 A1 | 3/2004 | Jenkins | |
| 2004/0181189 A1 | 9/2004 | Roychowdhury et al. | |
| 2004/0215181 A1 | 10/2004 | Christopherson | |
| 2005/0033285 A1 | 2/2005 | Swanson | |
| 2005/0055019 A1 | 3/2005 | Skarda | |

* cited by examiner

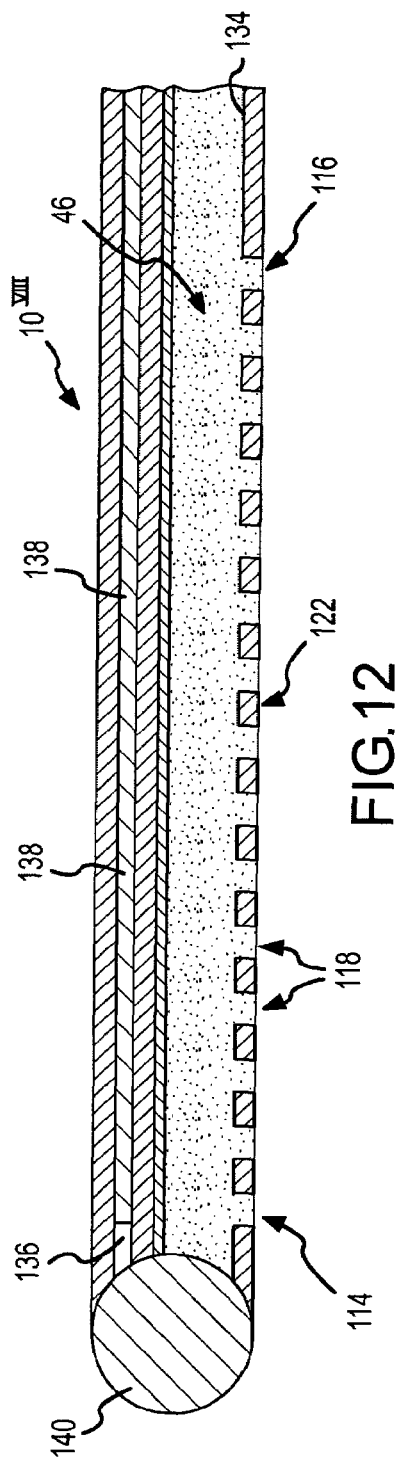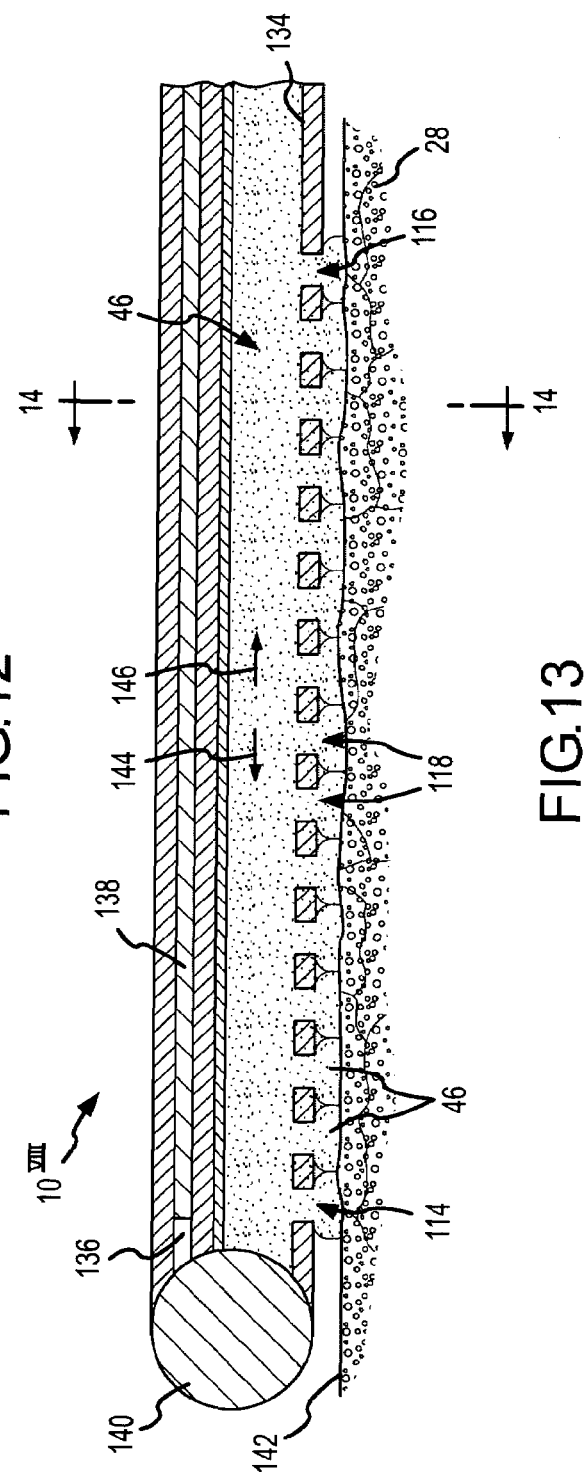

TREATMENT AND DIAGNOSTIC CATHETERS WITH HYDROGEL ELECTRODES

BACKGROUND OF THE INVENTION a. Field of the Invention

The instant invention is directed toward hydrogel electrode catheters for treatment and diagnosis of tissue. More specifically, the instant invention relates to treatment and diagnostic catheters with hydrogel virtual and sensing electrodes.

b. Background Art

Catheters have been in use for medical procedures for many years. Catheters can be used for medical procedures to examine, diagnose, and treat tissue while positioned at a specific location within the body that is otherwise inaccessible without more invasive procedures (e.g., medical procedures involving the human heart). During these procedures a catheter is inserted into a vessel located near the surface of a human body (e.g., an artery or vein in the leg, neck, or arm of the patient) and is guided or threaded through the vessels, sometimes with the aid of a guidewire or introducer, to a specific location within the body for examination, diagnosis, and treatment. For example, one procedure often referred to as "ablation" utilizes a catheter to convey energy (e.g., electrical or thermal) or a chemical to a selected location within the human body to create necrosis, which cuts off the path for stray or improper electrical signals. Another procedure often referred to as "mapping" utilizes a catheter with one or more sensing electrodes to monitor various forms of electrical activity in the human body.

It is well known that benefits may be gained by forming lesions in tissue during catheter ablation if the depth and location of the lesions being formed can be controlled. In particular, it can be desirable to elevate tissue temperature to around 50° C. until lesions are formed via coagulation necrosis, which changes the electrical properties of the tissue. When sufficiently deep lesions are formed at specific locations in cardiac tissue via coagulation necrosis, undesirable atrial fibrillations may be lessened or eliminated. "Sufficiently deep" lesions means transmural lesions in some cardiac applications.

Several difficulties may be encountered, however, when attempting to form adequately-deep lesions at specific locations using some existing ablation electrodes. For example, when forming lesions with radiofrequency (RF) energy, high temperature gradients are often encountered in the vicinity of the electrode. At the edges of some existing electrodes are regions of very high current density, leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There are two main types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

During RF ablation, as the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue. Active temperature control may help, but the placement of thermocouples, for example, is tricky and setting the RF generator for a certain temperature becomes an empirical exercise as actual tissue temperatures are generally different from those recorded next to the electrode due to factors such as convection and catheter design.

Conventional mapping catheters may include, for example, a plurality of adjacent ring electrodes constructed from platinum or some other metal. Since mapping catheters are desirably disposable, incorporation of relatively expensive platinum electrodes may be disadvantageous.

Another difficulty encountered with existing ablation catheters and mapping catheters is how to ensure adequate tissue contact. For example, current techniques for creating linear lesions (the term "linear lesion" as used herein means an elongated, continuous or uninterrupted lesion, whether straight or curved and whether comprising a single line of ablation or a series of connected points or lines of ablation forming a track, that blocks electrical conduction) in endocardial applications may include dragging a conventional catheter on the tissue, using an array electrode, or using preformed electrodes. All of these devices comprise rigid electrodes that do not always conform to the tissue surface, especially when sharp gradients and undulations are present, such as at the ostium of the pulmonary vein in the left atrium and the isthmus of the right atrium. Consequently, continuous linear lesions are difficult to achieve. Whether forming lesions or mapping in a heart, the beating of the heart, especially if erratic or irregular, further complicates matters, making it difficult to keep adequate contact between electrodes and tissue for a sufficient length of time. For example, with a rigid electrode, it can be quite difficult to maintain sufficient contact pressure during lesion formation until an adequate lesion has been formed. These problems are exacerbated on contoured or trabeculated surfaces. If the contact between electrodes and tissue cannot be properly maintained, quality lesions or accurate mapping are unlikely to result.

Catheters based upon a virtual electrode that deliver RF energy via conductive fluid flowing into the patient's body address some of the difficulties with ablation catheters, but these ablation catheters often require high flow rates of the conductive fluid (e.g., typically around 70 milliliters per minute) to maintain effective cooling for high-power RF applications. The introduction of a large amount of conductive fluid into a patient's bloodstream may have detrimental effects on the patient.

Thus, there remains a need for ablation catheters and mapping catheters that address these issues with the existing designs.

BRIEF SUMMARY OF THE INVENTION

Accordingly, it is an object of the disclosed invention to provide improved treatment and diagnostic catheters.

In one form, the present invention comprises a catheter for treatment of tissue, the catheter comprising at least one conductive hydrogel virtual electrode adapted to contact the tissue to be treated. In this form, the catheter includes a distal portion that comprises a straight section; a hoop-shaped section; an offset that joins the straight section to the hoop-shaped section; an active region along the hoop-shaped section; and a hydrogel delivery feature along the active region, wherein the hydrogel delivery feature is adapted to be placed against the tissue to be treated. The hoop-shaped section may define a distally-facing surface, and the hydrogel delivery feature may be on that distally-facing surface. Alternatively, the hoop-shaped section may define a radially outer peripheral wall that includes an outwardly-facing surface, and the hydrogel delivery feature may be on that outwardly-facing surface. The hydrogel delivery feature comprises at least one opening extending through the distally-facing surface or the outwardly-facing surface. The at least one opening may comprise, for example, a single row of hydrogel portholes, a plurality of rows of hydrogel portholes radially, a single hydrogel slot, or a plurality of hydrogel slots. The at least one opening my be centered about a radial apex of the distally-facing surface or of the outwardly-facing surface.

In another form, the present invention again comprises a catheter for treatment of tissue, the catheter comprising at least one conductive hydrogel virtual electrode adapted to contact the tissue to be treated. In this form, the catheter includes a distal portion that comprises a straight active region, the straight active region extending parallel to a catheter longitudinal axis; and a hydrogel delivery feature along the straight active region, the hydrogel delivery feature being adapted to be placed against the tissue to be treated. The straight active region defines an outer peripheral wall, wherein the outer peripheral wall defines an outwardly-facing surface, wherein the hydrogel delivery feature is on the outwardly-facing surface. The hydrogel delivery feature comprises at least one opening extending through the outer peripheral wall and its outwardly-facing surface. The at least one opening may comprise, for example, a single row of hydrogel portholes, a plurality of rows of hydrogel portholes radially, a single hydrogel slot, or a plurality of hydrogel slots. The at least one opening may be centered about a radial apex of the outwardly-facing surface.

In yet another form, the present invention comprises a catheter for treatment of tissue, the catheter comprising at least one conductive hydrogel virtual electrode, wherein the at least one conductive hydrogel virtual electrode is contained within a permeable or semi-permeable containment membrane adapted to contact the tissue to be treated. The membrane may comprise a shaped membrane adapted to take a predetermined configuration when filled with conductive hydrogel. For example, the containment membrane, when filled with conductive hydrogel, may be adapted to form a protuberance having a conformable surface to contact the tissue to be treated. This protuberance may take the shape of a hemisphere, a knob, a flattened gob, a hook, or a hoop.

In another form, the present invention comprises a drug delivery catheter for treatment of cardiac arrhythmias. In this embodiment, the catheter comprising a distal portion having an active region; a lumen extending inside the catheter adjacent to the active region; and a hydrogel delivery feature along the active region and in fluid communication with the lumen, wherein the hydrogel delivery feature is adapted to be placed against arrhythmia-producing, cardiac tissue inside of a heart. A conductive hydrogel matrix is present in the lumen, wherein the conductive hydrogel matrix is loaded with, for example, a water-soluble and ionic dispensable drug formulation. The hydrogel delivery feature may comprise, for example, a plurality of hydrogel portholes; and a permeable membrane attached at the plurality of hydrogel portholes and adapted to be alternatingly extendable out of and retractable back into the plurality of hydrogel portholes, wherein the membrane is adapted to contain the conductive hydrogel matrix, wherein the membrane is adapted to make contact with the cardiac tissue, and wherein the membrane is adapted to be traversable by the drug formulation.

In still another form, the present invention comprises a drug delivery system for treatment of cardiac arrhythmias. The system comprises a catheter having a distal portion. The distal portion of the catheter comprises an active region; a lumen extending adjacent to the active region, the lumen being adapted to contain a conductive hydrogel matrix loaded with, for example, a water-soluble and ionic dispensable drug formulation; and a hydrogel delivery feature. The hydrogel delivery feature comprises an opening through the active region, the opening being in fluid communication with the lumen and being adapted to be placed against arrhythmia-producing, cardiac tissue; and a permeable membrane attached at the opening and adapted to be alternatingly extendable out of and retractable back into the opening, wherein the membrane is adapted to contain the conductive hydrogel matrix, wherein the membrane is adapted to make contact with the cardiac tissue, and wherein the membrane is adapted to be traversable by the ionic dispensable drug formulation. In this embodiment, the system also comprises a current supply adapted to deliver low-intensity direct current to the conductive hydrogel matrix. The opening through the sidewall of the catheter may comprise, for example, at least one hydrogel porthole or at least one hydrogel slot.

In another form, the present invention comprises a diagnostic catheter for diagnosing cardiac tissue, the catheter comprising at least one conductive hydrogel sensing electrode. The at least one conductive hydrogel sensing electrode may comprise a plurality of isolated, conductive hydrogel disks that are electrically separated by nonconductive hydrogel disks. These conductive and nonconductive hydrogel disks may be constructed from, for example, high-viscosity, rigid hydrogel that is substantially unaffected by moisture. The conductive hydrogel disks may be adhered to the nonconductive hydrogel disks. In this embodiment, each of the plurality of conductive hydrogel disks is electrically connected with a separate electrical lead (e.g., a silver or silver-chloride coated wire) for transmitting electrical signals from the treatment site to instrumentation outside of a patient's body.

In yet another form, the present invention comprises a method of treating cardiac tissue. The method comprises the steps of guiding an ablation catheter having at least one conductive hydrogel virtual electrode to the cardiac tissue to be treated; introducing the at least one conductive hydrogel virtual electrode against the cardiac tissue; and directing ablative energy to the cardiac tissue via the at least one conductive hydrogel virtual electrode.

In still another form, the present invention comprises a method of treating cardiac tissue, the method comprising the steps of filling at least a distal portion of a catheter lumen with conductive hydrogel, the catheter lumen extending adjacent to a catheter active region on a catheter outer surface; guiding the catheter active region into contact with the cardiac tissue to be treated; activating a hydrogel displacement device to advance the conductive hydrogel toward the active region until the conductive hydrogel broaches the catheter outer surface to thereby introduce at least one conductive hydrogel virtual electrode against the cardiac tissue; directing ablative energy through the at least one conductive hydrogel virtual electrode and into the cardiac tissue; and activating the hydrogel displacement device to retract the conductive hydrogel and thus the at least one conductive hydrogel virtual electrode from contact with the cardiac tissue and back into the catheter lumen.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 12 is a fragmentary, cross-sectional view taken along line 12-12 of FIG. 10, shown with the conductive hydrogel poised at the hydrogel porthole exits prior to being forced to protrude from the portholes.

FIG. 13 is similar to FIG. 12, but depicts the conductive hydrogel in its deployed configuration, protruding from the portholes against the tissue to be treated.

DETAILED DESCRIPTION OF THE INVENTION

Figure 20:
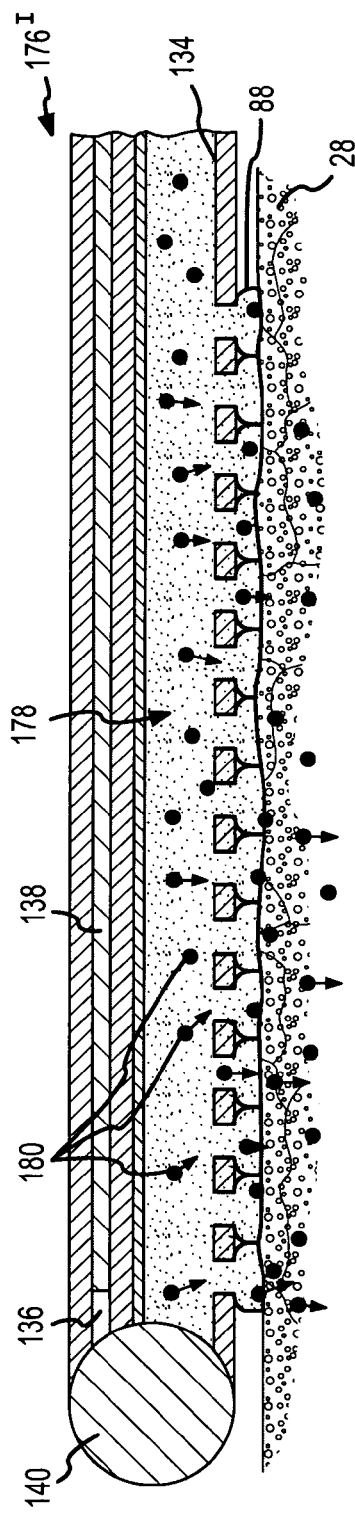
FIG. 20 is a fragmentary, cross-sectional view of the distal portion of a hydrogel drug delivery catheter according to an eleventh embodiment of the present invention.
Figure 21:
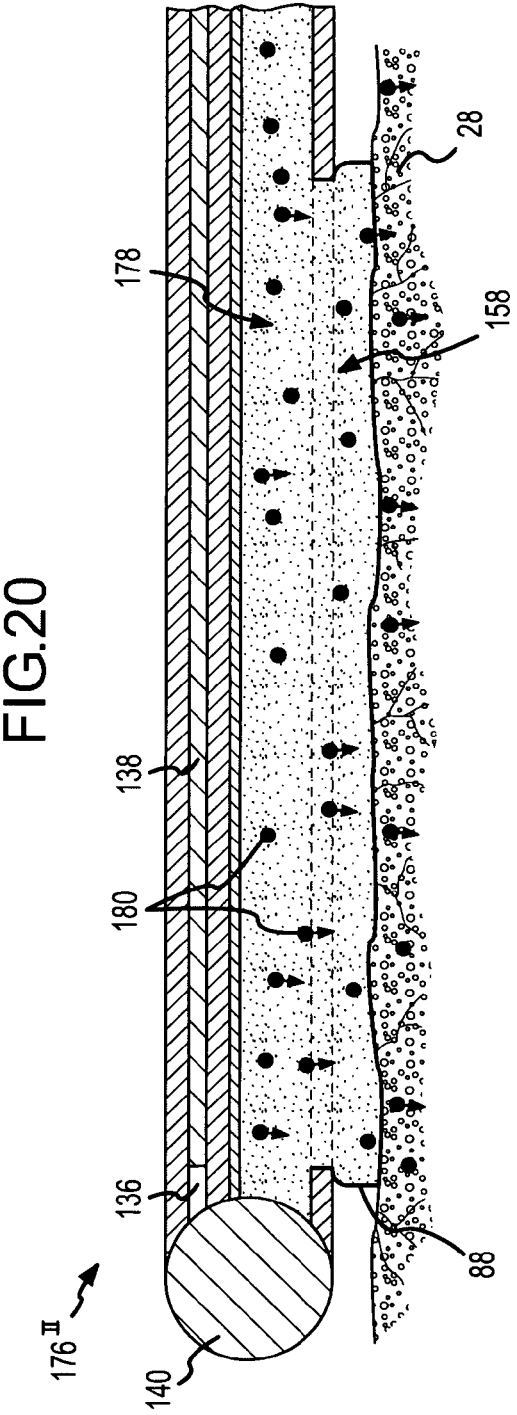
FIG. 21 is a fragmentary, cross-sectional view of the distal portion of a hydrogel drug delivery catheter according to a twelfth embodiment of the present invention.
Figure 22:
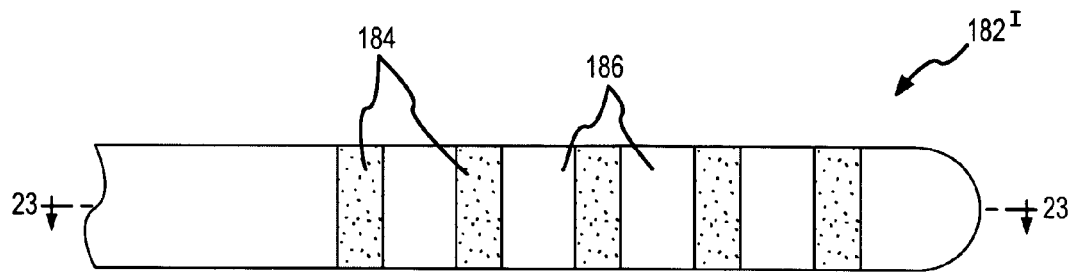
FIG. 22 is a fragmentary, top view of the distal portion of a diagnostic catheter according to a thirteenth embodiment of the present invention.
Figure 23:
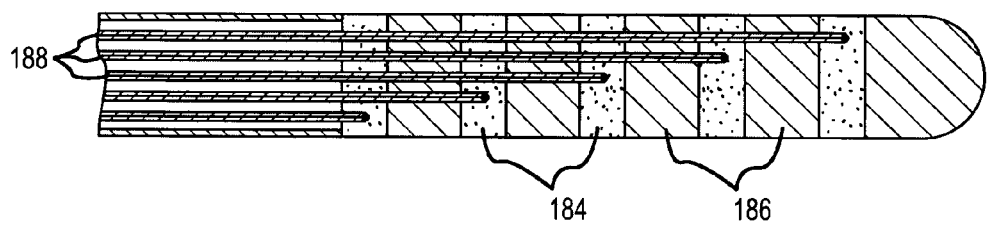
FIG. 23 is a fragmentary, cross-sectional view taken along line 23-23 of FIG. 22.
Figure 24:
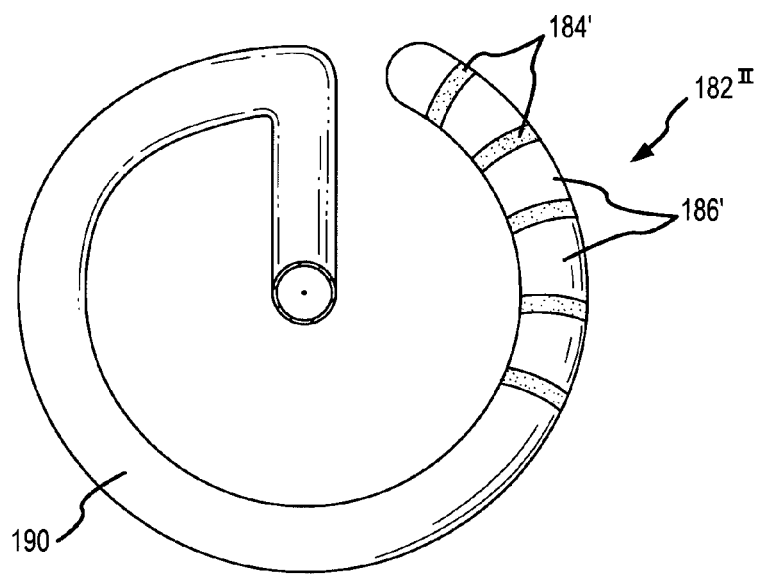
FIG. 24 is a fragmentary, end view (looking distally) of the distal portion of a diagnostic catheter according to a fourteenth embodiment of the present invention.

The present invention comprises a variety of catheters with hydrogel virtual electrodes for treatment and diagnosis of tissue (e.g., human cardiac tissue). In particular, FIGS. 1-19 depict a number of different configurations for hydrogel virtual electrode ablation catheters, FIGS. 20 and 21 depict hydrogel drug delivery catheters, and FIGS. 22-24 depict hydrogel diagnostic catheters. Whenever there may be contact between the hydrogel and a patient's blood, each of the catheters depicted in FIGS. 1-24 uses hemocompatible hydrogel that may or may not be radiopaque. Viscoelastic hydrogel, for example, may be used in the treatment catheters depicted in FIGS. 1-21; and a high-viscosity, rigid hydrogel that is substantially unaffected by moisture (e.g., a hydrogel that does not swell in the presence of moisture) may be used in the diagnostic catheters depicted in FIGS. 22-24. In all of the embodiments depicted and described herein, the hydrogel does not enter a patient's bloodstream in any appreciable amounts. The portholes, slots, and openings depicted in FIGS. 1-21 are adapted to allow the hydrogel to be alternatingly forced from and retracted back into the catheter using a hydrogel displacement device such as a plunger, a pump, or a syringe, none of which are shown in the drawings. For example, a screw-, gear-, or piston-pump may be used to move the hydrogel under whatever pressure is required (e.g., 500 psi).

Figure 1:
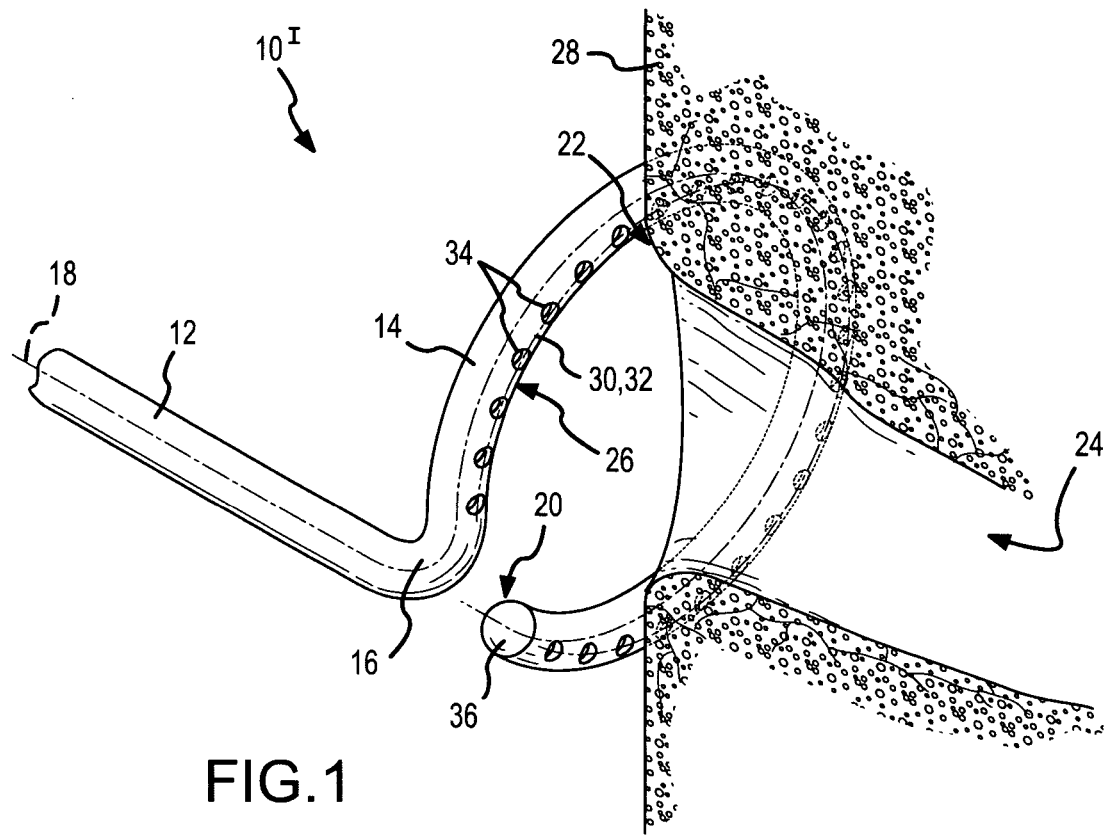
FIG. 1 is fragmentary, isometric view of the distal portion of an ablation catheter according to a first embodiment of the present invention adjacent to the ostium of a pulmonary vein.

FIG. 1 is a fragmentary, isometric view of the distal portion $10'$ of an ablation catheter according to a first embodiment of the present invention. In this embodiment, the distal portion $10'$ of the ablation catheter comprises a straight section 12 and a curved or hoop-shaped section 14 that are joined at a bend or offset 16. A longitudinal axis 18 extends through both the straight section 12 and the curved section 14. As used herein, the term "longitudinal axis" refers to the longitudinal axis extending through the straight section 12 and through the curved section 14 of the ablation catheter, from the proximal end (not shown) of the catheter to the distal end 20 of the ablation catheter. The curved or hoop-shaped section 14 is C-shaped as shown, but may define a completely circular configuration rather than the open, C-shape depicted in FIG. 1. The bend or offset 16 may be formed or configured as shown in FIG. 1, wherein the offset displaces the straight section 12 of the catheter to the side, causing the straight section 12 to meet the curved section 14 of the catheter along the perimeter of the hoop-shaped curved section 14 (i.e., substantially perpendicularly to the plane containing the C-shaped curved section 14 and along the imaginary cylindrical surface formed by sliding the C-shaped curved section parallel to the longitudinal axis 18 of the straight section 20 to create a substantially cylindrical surface). Alternatively, the offset 78 (e.g., FIGS. 5-7) may be configured so that the straight section 84 approaches the plane containing the C-shaped or hoop-shaped curved section 78 near the center of the "C" or hoop (see, e.g., FIG. 6). The "straight section" 84 of the catheter shaft is "straight" relative to the C-shaped or hoop-shaped section 78, but remains flexible enough to be navigated through a patient's vasculature to a treatment site (e.g., the ostium 22 of a pulmonary vein 24 as shown in FIG. 1).

The curved section 14 of the ablation catheter defines a distally-facing surface 26. As shown in FIG. 1, the distally-facing surface 26 is placed against the tissue 28 to be treated (e.g., the ostium 22 of a pulmonary vein 24 as shown in FIG. 1). In the embodiment depicted in FIG. 1, the distally-facing surface 26 defines a distally-facing radial apex 30. The distally-facing radial apex is the most distal surface of the curved section 14 of the ablation catheter. In FIG. 1, the distally-facing radial apex 30 defines a C-shaped line which, in the embodiment depicted in FIG. 1, overlies a porthole centerline 32 for a plurality of distally-facing hydrogel portholes 34. In particular, the ablation catheter depicted in FIG. 1 includes a hydrogel deployment feature comprising a single row of hydrogel portholes 34 centered along the porthole centerline 32 on the radial apex 30 of the distally-facing surface 26. In the configuration depicted in FIG. 1, the conductive hydrogel used to treat the tissue remains inside the distal portion $10^I$ of the ablation catheter and has not yet been forced to protrude through the hydrogel portholes 34 into contact with the tissue 28 to be treated. As shown in FIG. 1, the ablation catheter may also include a rounded tip 36, which may or may not be conductive.

Figure 2:
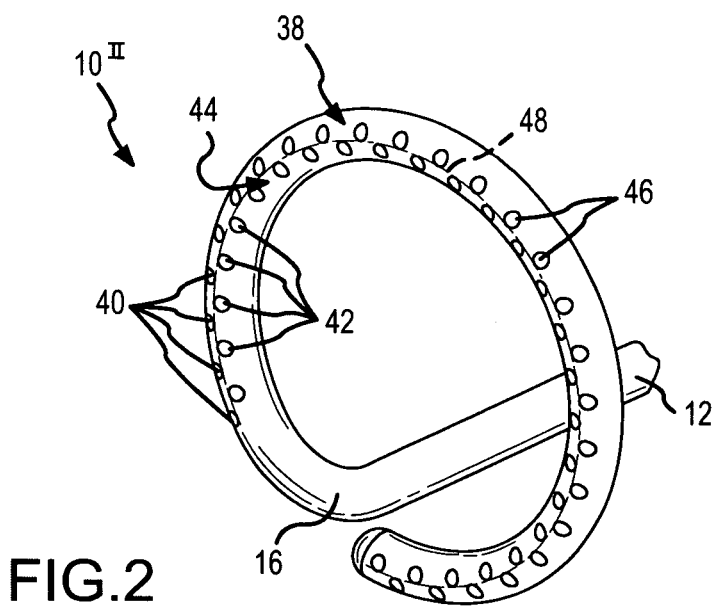
FIG. 2 is a fragmentary, isometric view of the distal portion of an ablation catheter according to a second embodiment of the present invention.

FIG. 2 is a fragmentary, isometric view of the distal portion $10^{II}$ of an ablation catheter according to a second embodiment of the present invention. Similar to the embodiment $10^I$ depicted in FIG. 1, the ablation catheter depicted in FIG. 2 comprises a straight section 12 and a curved section 38 joined by a bend or offset 16. In the embodiment $10^{II}$ depicted in FIG. 2, the hydrogel deployment feature comprises concentric arcs of staggered hydrogel portholes, including a first plurality of hydrogel portholes 40 along an outer arc and a second plurality of hydrogel portholes 42 along an inner arc. Thus, in the embodiment depicted in FIG. 2, the hydrogel deployment feature is again on the distally-facing surface 44 of the distal portion $10^{II}$ of the ablation catheter. In the configuration depicted in FIG. 2, the conductive hydrogel 46 has been pushed distally in the catheter until it is flush with the outer surface of the curved section where each hydrogel porthole 40,42 broaches the outer surface of the catheter. Thus, the conductive hydrogel 46, if forced distally any further, will protrude from the hydrogel portholes 40,42, distally away from the distally-facing surface 44 of the ablation catheter, as discussed further below.

The concentric arcs of staggered hydrogel portholes comprise a plurality of hydrogel portholes on alternating sides of a porthole centerline 48, thereby forming a zigzagging row of hydrogel portholes 40,42. In general, the hydrogel porthole configuration depicted in FIG. 2 may be used to make a wider arcuate, linear lesion than the lesion that may be formed by the single row of hydrogel portholes 34 depicted in FIG. 1 without greatly changing the size of each individual porthole. By staggering the portholes 40 of the outer arc of hydrogel portholes relative to the portholes 42 of the inner arc of hydrogel portholes, it is possible to reduce opportunities for gaps to exist in the lesion formed during treatment. Lesion formation is discussed further below.

Figure 3:
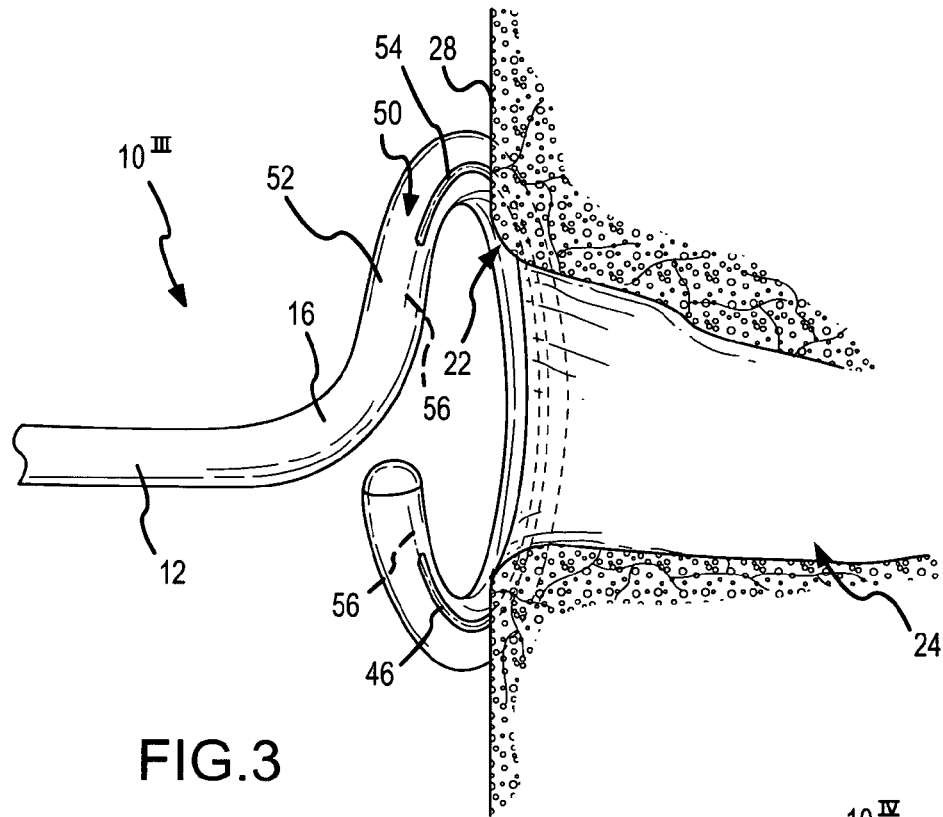
FIG. 3 is a fragmentary, isometric view of the distal portion of an ablation catheter according to a third embodiment of the present invention depicted next to the ostium of a pulmonary vein.

FIG. 3 is a fragmentary, isometric view of the distal portion $10^{III}$ of an ablation catheter according to a third embodiment of the present invention. Similar to what is depicted in FIG. 1, FIG. 3 depicts the distally-facing surface 50 of the distal portion $10^{III}$ of the ablation catheter at the ostium 22 of a pulmonary vein 24. In this embodiment, the distal portion $10^{III}$ of the ablation catheter again includes a straight section 12 and a curved section 52 joined by a bend or offset 16. Similar to the embodiments depicted in FIGS. 1 and 2, the embodiment of FIG. 3 also comprises a hydrogel deployment feature on the distally-facing surface 50 of the curved section 52 of the catheter. In the third embodiment, the hydrogel portholes 34, 40, 42 of FIGS. 1 and 2 have been replaced by a longitudinally-extending hydrogel slot 54 that straddles a slot centerline 56 on the radial apex of the distally-facing surface 50. Again, as was shown in FIG. 2, in the configuration depicted in FIG. 3, the conductive hydrogel 46 fills the longitudinally-extending hydrogel slot 54, flush with the distally-facing surface 50 of the ablation catheter, but does not yet protrude outwardly through the hydrogel slot 54. If the tissue 28 to be treated has a relatively flat surface, ablative energy may be applied to the tissue while the conductive hydrogel 46 is in this flush, non-protruding configuration. As discussed further below, however, if the tissue 28 to be ablated comprises trabeculations or undulations, the column or segment of conductive hydrogel in the catheter may be forced distally until the conductive hydrogel 46 actually protrudes from the longitudinally-extending hydrogel slot 54 so that the conductive hydrogel 46 has an opportunity to conform to the trabeculated tissue surface (see, e.g., FIGS. 13 and 14).

Figure 4:
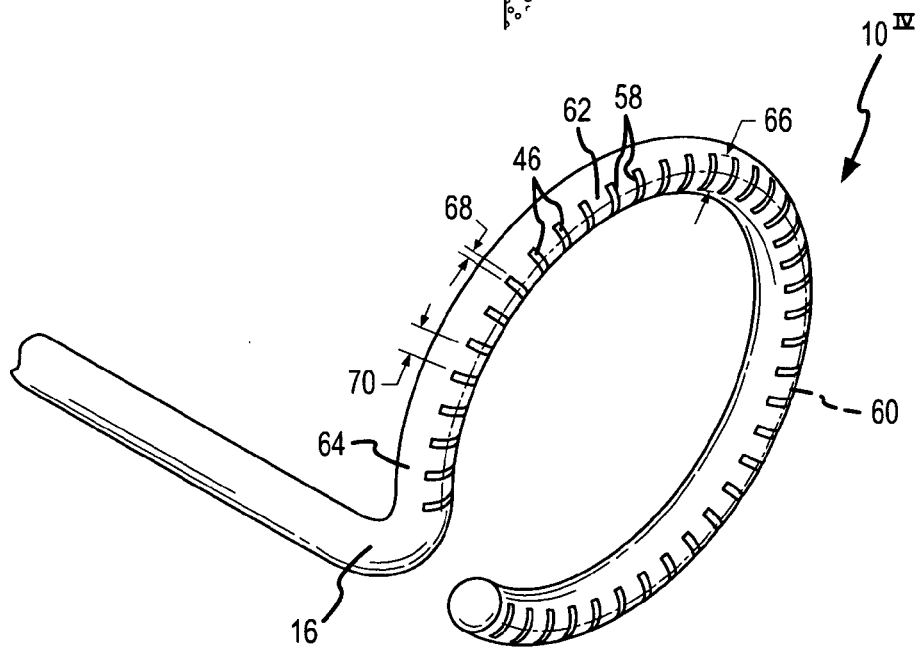
FIG. 4 is a fragmentary, isometric view of the distal portion of an ablation catheter according to a fourth embodiment of the present invention.

FIG. 4 is a fragmentary, isometric view of the distal portion $10^{IV}$ of an ablation catheter according to a fourth embodiment of the present invention. The embodiment depicted in FIG. 4 is similar to the embodiments depicted in FIGS. 1-3, except for the hydrogel deployment feature. In FIG. 4, the conductive hydrogel 46 is deployed or delivered through the catheter and against the tissue 28 being ablated via a plurality of laterally-extending or transversely-extending hydrogel slots 58. These laterally-extending hydrogel slots 58 extend substantially perpendicularly to the arc or line defining a slot centerline 60 along the radial apex of the distally-facing surface 62 of the curved section 64 of the ablation catheter. The transverse length 66 of each hydrogel slot 58 may be adjusted to obtain the desired lesion width. The longitudinal width 68 of each hydrogel slot 58 as well as the separation distance 70 between adjacent slots may be adjusted to control potential gaps in the arcuate lesion formed during use of the ablation catheter depicted in FIG. 4. Similar to what is depicted in FIGS. 2 and 3, the conductive hydrogel 46 depicted in FIG. 4 has been advanced distally until the hydrogel 46 is flush with the distally-facing surface 62 of the ablation catheter where the laterally-extending hydrogel slots 58 pierce or broach the outer surface of the curved section 64 of the ablation catheter.

Figure 5:
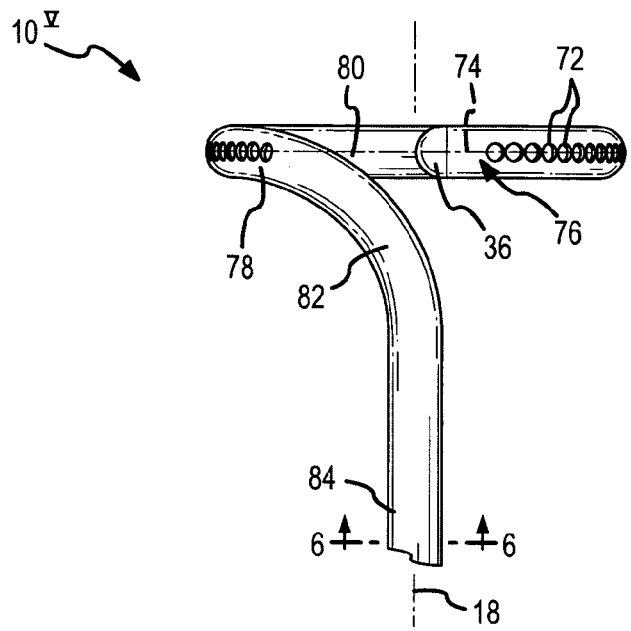
FIG. 5 is a fragmentary, top view of the distal portion of an ablation catheter according to a fifth embodiment of the present invention.
Figures 6, 7:
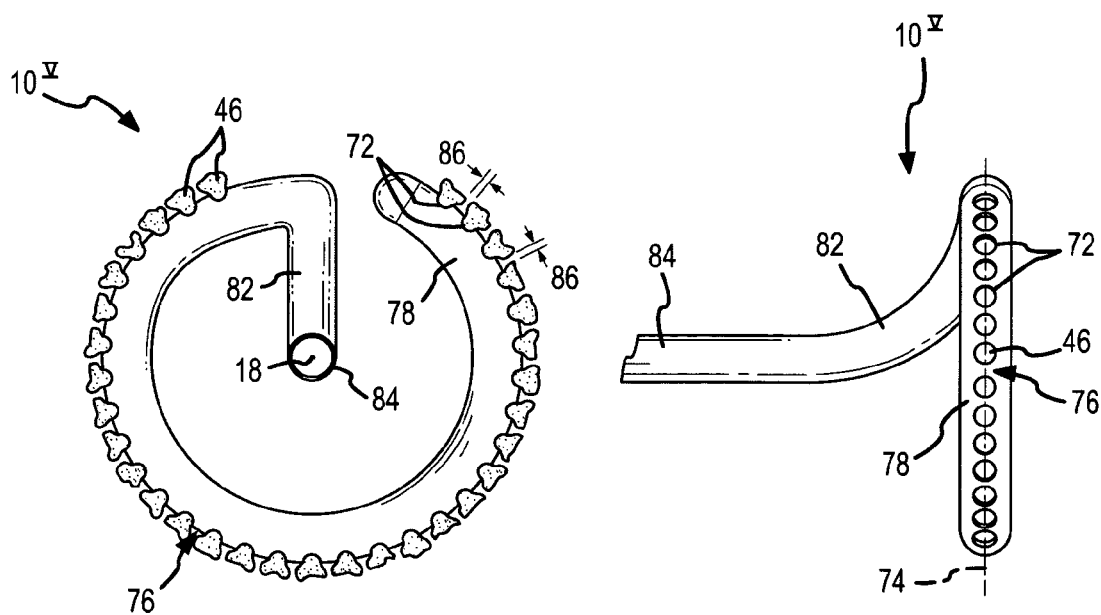
FIG. 6 is a fragmentary, end view (looking distally) of the ablation catheter depicted in FIG. 5, shown with at least partially deployed conductive hydrogel protruding from the hydrogel portholes.
FIG. 7 is a fragmentary, side view of the ablation catheter depicted in FIGS. 5 and 6, shown with the conductive hydrogel retracted into the catheter.

FIGS. 5-7 are fragmentary views of the distal portion $10^V$ of an ablation catheter according to a fifth embodiment of the present invention. In the embodiment depicted in FIGS. 5-7, the hydrogel deployment feature comprises a plurality of hydrogel portholes 72 arranged along a single row, similar to the plurality of portholes 34 depicted in FIG. 1. In the embodiment of FIGS. 5-7, however, the single row of hydrogel portholes 72 is present along a porthole centerline 74 on the radial apex of an outer peripheral wall 76 of the curved section 78 rather than being on the radial apex 30 of the distally-facing surface 26 as shown in FIG. 1. In other words, the ablation catheter depicted in FIGS. 5-7 comprises an inner peripheral wall 80 and an outer peripheral wall 76 on the hoop-shaped or curved section 78, and the portholes 72 extend substantially radially through the outer peripheral wall 76 of this C-shaped or hoop-shaped curved section 78 of the ablation catheter.

FIG. 6 is a fragmentary, end view (looking distally) at the distal portion $10^V$ of the ablation catheter depicted in FIG. 5, shown with at least partially deployed conductive hydrogel 46 protruding from the hydrogel portholes 72; and FIG. 7 is a fragmentary, side view of the ablation catheter depicted in FIGS. 5 and 6, shown with the conductive hydrogel 46 retracted into the catheter. As depicted to best advantage in FIGS. 6 and 7, this fifth embodiment of the ablation catheter also includes an offset 82 that is slightly different from the offset 16 depicted in FIGS. 1-4. In particular, the offset 82 depicted in FIGS. 5-7 places the straight section 84 of the catheter shaft so that, if extended distally, the distal end of the straight section 84 would pass through a plane containing the C-shaped or hoop-shaped curved section 78 of the distal portion 10$^V$ of the ablation catheter at nearly the center of the C-shaped or hoop-shaped curved section 78. Since the hydrogel portholes 72 of this embodiment pass through the outer peripheral wall 76, this version of the ablation catheter may be inserted inside of a pulmonary vein 24, for example, rather than being placed at the ostium 22 of a pulmonary vein 24 as depicted in FIGS. 1 and 3. Since this version 10$^V$ of the ablation catheter may be placed inside of a pulmonary vein 24, configuring the offset 82 to displace the straight section 84 toward the center of the C-shaped curved section 78 results in a configuration that places the straight section 84 of the catheter shaft away from the wall of, for example, a pulmonary vein 24 into which the ablation catheter has been inserted to treat tissue 28.

In FIG. 5, the conductive hydrogel is undeployed. In FIG. 6, on the other hand, the conductive hydrogel 46 has been at least partially deployed and protrudes from each of the hydrogel portholes 72. Ablative energy (e.g., RF energy) may be applied to the hydrogel 46 in its at least partially deployed configuration depicted in FIG. 6. If desired, additional hydrogel may be deployed from the hydrogel portholes 72 until the protruding portions of hydrogel 46 touch any adjacent protruding portions of hydrogel 46 thereby eliminating gaps 86. By thus controlling the amount of conductive hydrogel 46 protruding from the hydrogel portholes 72, it is possible to control potential gaps in a linear lesion formed by the ablative energy passing through the protruding conductive hydrogel 46. As shown in FIG. 6, the conductive hydrogel 46 itself may come into contact with the tissue 28 (see, e.g., FIGS. 1 and 3) to be treated. Alternatively, as described below in connection with, for example, FIG. 15, the conductive hydrogel 46, in all of the embodiments, may be contained within a permeable or semi-permeable containment bag or liner or membrane 88. In these latter configurations, the containment membrane 88 makes the actual contact with the tissue 28 to be treated rather than the conductive hydrogel 46 itself.

Figure 8:
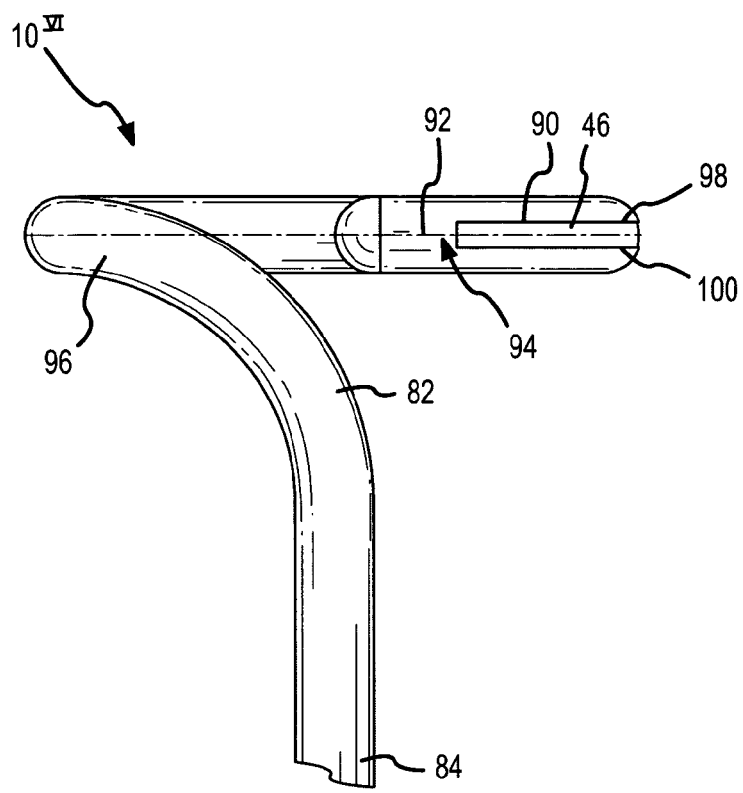
FIG. 8 is a fragmentary, top view of the distal portion of an ablation catheter according to a sixth embodiment of the present invention.

FIG. 8 is a fragmentary, top view of the distal portion 10$^{VI}$ of an ablation catheter according to a sixth embodiment of the present invention. This embodiment is similar to the embodiment depicted in FIGS. 5-7, but the plurality of hydrogel portholes 72 have been replaced with a longitudinally-extending hydrogel slot 90 as the hydrogel deployment feature. This longitudinally-extending hydrogel slot 90 straddles a slot centerline 92 along the radial apex of the outer peripheral wall 94 of the curved section 96 of the distal portion 10$^{VI}$ of the ablation catheter. The longitudinally-extending hydrogel slot 90 is present between a distal slot edge 98 and a proximal slot edge 100. The longitudinally-extending hydrogel slot 90 depicted in FIG. 8 is similar to the longitudinally-extending hydrogel slot 54 depicted in FIG. 3; however, the slot 90 depicted in FIG. 8 extends through the outer peripheral wall 94 of the curved section 96 rather than through the distally-facing surface 50 of the curved section 52 (FIG. 3). Thus, the ablation catheter depicted in FIG. 8 is again configured for use inside, for example, a pulmonary vein 24 so that the conductive hydrogel 46 extending into or through the longitudinally-extending hydrogel slot 90 would come into contact with the tissue 28 to be treated. With this type of target use, the ablation catheter depicted in FIG. 8 may again comprise an offset 82 that places the straight section 84 of the catheter shaft central to the curved, C-shaped or hoop-shaped section 96 as discussed in connection with FIGS. 5-7.

Figure 9:
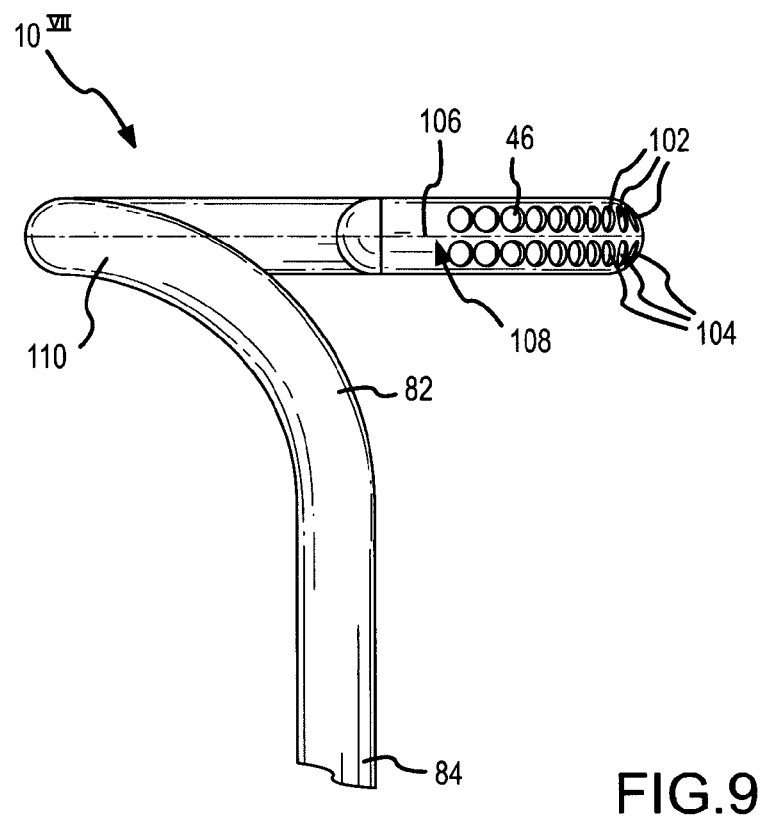
FIG. 9 is a fragmentary, top view of the distal portion of an ablation catheter according to a seventh embodiment of the present invention.

FIG. 9 is a fragmentary, top view of the distal portion 10$^{VII}$ of an ablation catheter according to a seventh embodiment of the present invention. In this embodiment, the hydrogel 46 is delivered adjacent to or against the tissue 28 to be ablated via a hydrogel deployment feature comprising a first plurality of hydrogel portholes 102 arranged in a distal arc and a second plurality of hydrogel portholes 104 arranged in a proximal arc. These arcs of portholes symmetrically straddle a porthole centerline 106 along the radial apex of the outer peripheral wall 108 of the curved section 110 of the distal portion 10$^{VII}$ of the ablation catheter, and, in the specific configuration depicted in FIG. 9, each hydrogel porthole 102 of the distal arc has a corresponding hydrogel porthole 104 along the proximal arc. These two arcs of portholes could be offset or staggered, similar to what is shown in FIG. 2. In the embodiment of FIG. 9, however, the portholes 102, 104 extend through the outer peripheral wall 108 of the curved section 110 of the distal portion 10$^{VII}$ of the ablation catheter rather than through the distally-facing surface 44 of the distal portion 10$^{II}$ of the ablation catheter as shown in FIG. 2. Also, more than two arcs of hydrogel portholes may be present. For example, a third, intermediate arc of hydrogel portholes (not shown) may be present between the hydrogel portholes 102 of the distal arc and the hydrogel portholes 104 of the proximal arc depicted in FIG. 9.

Figure 10:
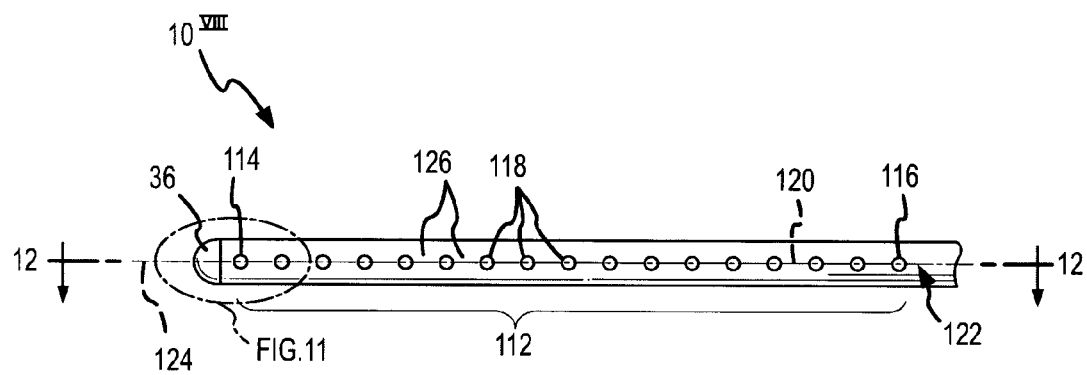
FIG. 10 is a fragmentary, top view of the distal portion of an ablation catheter according to an eighth embodiment of the present invention.

FIG. 10 is a fragmentary, top view of the distal portion 10$^{VIII}$ of an ablation catheter according to an eighth embodiment of the present invention. The embodiment 10$^{VIII}$ depicted in FIG. 10 is similar to the fifth embodiment 10$^V$ depicted in FIGS. 5-7. In FIG. 10, however, the portion of the catheter comprising the hydrogel deployment feature (i.e., the plurality of hydrogel portholes along the active region 112 of the catheter) is relatively straight and not C-shaped or hoop-shaped. The plurality of hydrogel portholes includes a most distal porthole 114, a most proximal porthole 116, and at least one intermediate porthole 118 arranged along a porthole centerline 120. These portholes 114, 116, 118 extend through an outer peripheral wall 122 of the distal portion 10$^{VIII}$ of the ablation catheter, substantially perpendicularly to the longitudinal axis 124 of the catheter.

Figure 11:
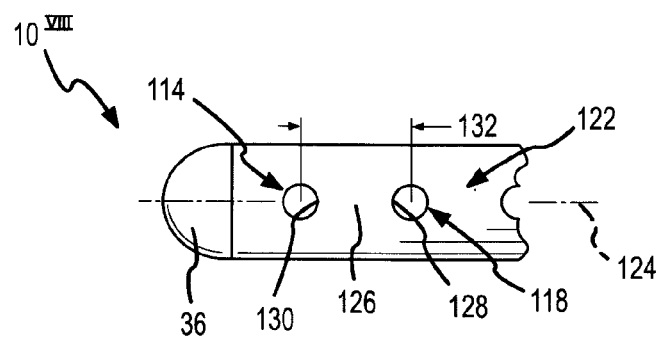
FIG. 11 is an enlarged, fragmentary view of the portion that is circled in FIG. 10.

FIG. 11 is an enlarged, fragmentary view of the portion that is circled by a dashed line in FIG. 10. As shown in FIG. 11, a bridge 126 is present between adjacent portholes (e.g., 114, 118, in FIG. 11). The width of the bridge is the distance between a distal trailing edge 128 of one porthole 118 and the proximal leading edge 130 of an adjacent porthole 114. Adjusting the distance 132 between adjacent portholes clearly affects the size of the bridge 126 between portholes. By adjusting the size of the bridges 126 and the size of the portholes 114, 116, 118 themselves, it is possible to attain a configuration for the ablation catheter to produce a linear lesion of a predetermined depth and length, and a lesion with or without gaps in it. Similar adjustments could be made to the hydrogel portholes depicted in any of the other figures.

FIG. 12 is a fragmentary, cross-sectional view taken along line 12-12 of FIG. 10. Visible for the first time in this figure is one possible cross-sectional configuration for the catheter shaft for all of the embodiments. In this configuration, the catheter shaft includes a first lumen 134 through which the conductive hydrogel 46 moves and a second lumen 136 containing a shape memory wire or a steering wire 138 used to position the hydrogel 46 deployment feature adjacent to the tissue 28 to be treated. In FIG. 12, the conductive hydrogel 46 is poised for deployment. In other words, the hydrogel 46 has been pushed distally in the catheter until the conductive hydrogel 46 is flush with the outer surface 122 of the ablation catheter. The conductive hydrogel remains within the hydrogel portholes 114, 116, 118, but may be placed adjacent to the tissue to be treated. Thus, as mentioned above, with the hydrogel thereby poised for deployment, if the active region 112 (FIG. 10) of the ablation catheter (i.e., the hydrogel portholes in the depicted embodiment) were placed against tissue to be treated, and if that tissue comprised a relatively flat surface, ablative energy may be transmitted to the tissue with the conductive hydrogel positioned as shown in FIG. 12. As previously mentioned, the rounded tip 36 of the catheter may or may not be conductive. If the rounded tip is nonconductive, it may comprise, for example, a sphere or "plug" of adhesive or polymer 140 that seals the end of the catheter lumen.

Figure 15:
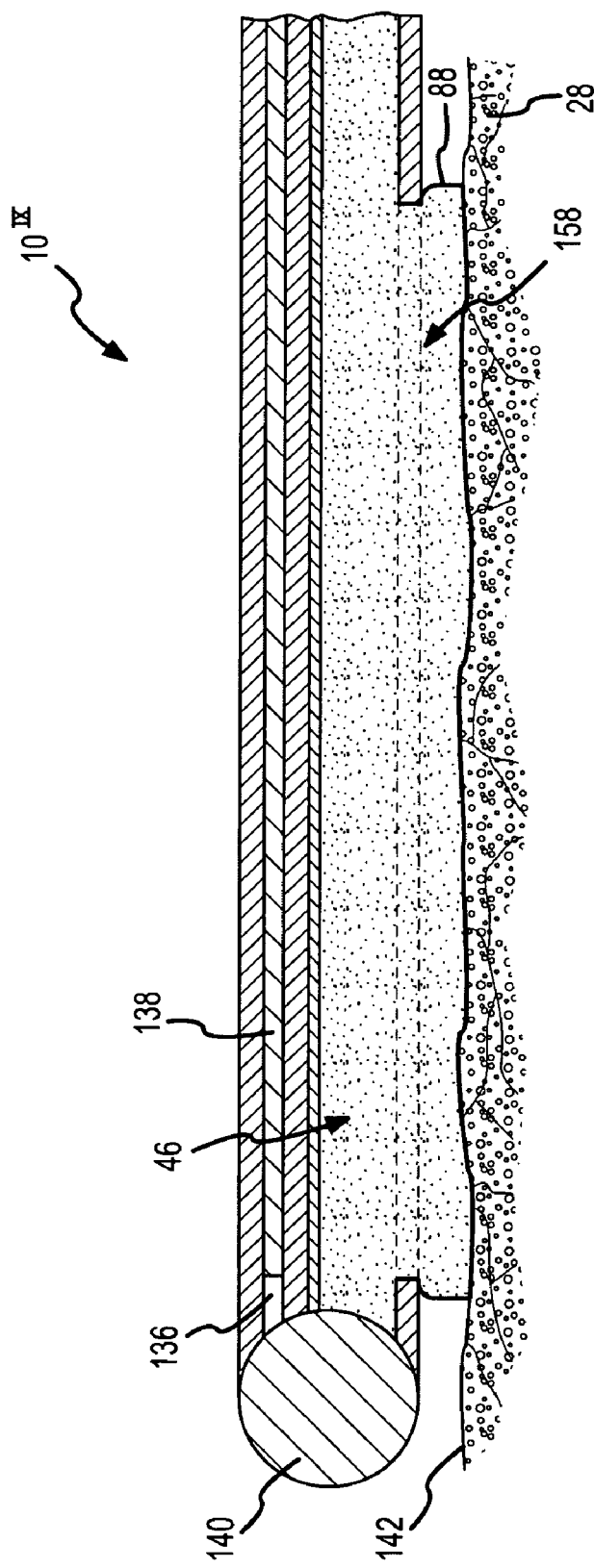
FIG. 15 is a fragmentary, cross-sectional view of the distal portion of an ablation catheter according to a ninth embodiment and depicts a membrane containing the protruding conductive hydrogel.

FIG. 13 is similar to FIG. 12, but depicts the conductive hydrogel 46 in its deployed configuration, protruding from the hydrogel portholes 114, 116, 118 against the tissue 28 to be treated. In order to facilitate better contact with the tissue 28 to be ablated, particularly when the surface 142 of the tissue 28 is trabeculated or undulated as shown in FIG. 13, and to help eliminate potential gaps in the lesion that is formed by the ablative energy delivered through the conductive hydrogel 46, the conductive hydrogel may be forced distally through the first lumen 134 (i.e., in the direction of arrow 144 in FIG. 13) of the catheter shaft until the portions of hydrogel protruding through each hydrogel porthole contact 114, 116, 118 adjacent portions of hydrogel as shown in FIG. 13. In the embodiment depicted in this figure, no containment bag or membrane or liner 88 is present (compare what is shown in FIG. 15, which includes a membrane 88); and the conductive hydrogel 46 itself directly contacts the tissue 28 being treated. Again, as previously mentioned, after the tissue treatment has been completed, the conductive hydrogel 46 is pulled or pumped back into the shaft of the ablation catheter (i.e., in the direction of arrow 146 in FIG. 13) before the catheter is extracted from the patient. Thus, very little, if any, conductive hydrogel 46 remains in the patient's body after the treatment is completed.

Figure 14:
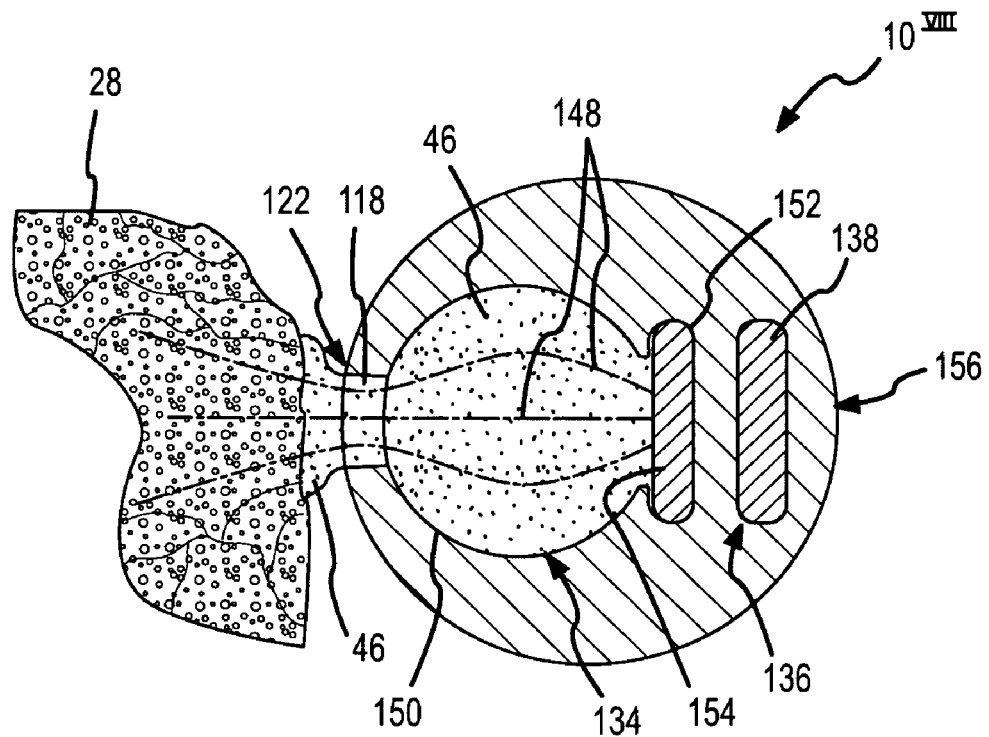
FIG. 14 is a fragmentary, cross-sectional view taken along line 14-14 of FIG. 13 and depicts ablative energy being transferred to the tissue through the conductive hydrogel.

FIG. 14 is a fragmentary, cross-sectional view taken along line 14-14 of FIG. 13 and depicts ablative energy 148 being transferred to the tissue 28 through the conductive hydrogel 46. This figure depicts additional details about one possible configuration for the catheter shaft. In this depicted configuration, the first lumen 134, through which the conductive hydrogel 46 is moved, comprises a nearly-circular subportion 150 and a rounded-rectangular subportion 152. The rounded-rectangular subportion 152 may be used to retain an electrode 154 that delivers ablative energy 148 (e.g., RF energy) through the conductive hydrogel 46 to the tissue 28 being treated. The second lumen 136, when present, may contain the shape memory wire or steering wire 138 used to position the hydrogel deployment feature of the ablation catheter adjacent to the tissue being treated and may permit the physician to manipulate the shape of the distal portion $10^{VIII}$ of the ablation catheter to better conform to the tissue being treated. In the embodiment depicted in FIG. 14, the second lumen 136 is adjacent to an inner peripheral wall 156 of the distal portion $10^{VIII}$ of the catheter.

FIG. 15 is a fragmentary, cross-sectional view of the distal portion $10^{IX}$ of an ablation catheter according to a ninth embodiment of the present invention. This cross-sectional view is similar to the cross-sectional view of FIG. 13, but depicts a hydrogel deployment feature comprising a longitudinally-extending hydrogel slot 158 (compare slot 54 in FIG. 3 and slot 90 in FIG. 8) and a flexible, permeable or semipermeable membrane 88 cooperating to deliver the conductive hydrogel 46 to the tissue 28 being treated. In the particular configuration depicted in FIG. 15, the protruding conductive hydrogel is contained within the flexible, permeable or semi-permeable membrane 88; and it is this membrane 88 that makes contact with the surface 142 of the tissue 28 being treated. This membrane may be used, for example, to facilitate hydrogel containment and/or to ensure that the conductive hydrogel 46 protruding from the distal portion of the ablation catheter takes a desired configuration as explained further below in connection with FIGS. 16-19.

Figure 16:
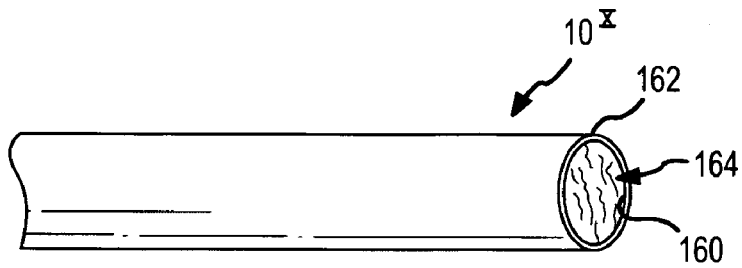
FIG. 16 is a fragmentary, top view of the distal portion of an ablation catheter according to a tenth embodiment of the present invention prior to deployment of the conductive hydrogel.

FIGS. 16-19 are fragmentary, isometric top views of the distal portion $10^X$ of an ablation catheter according to a tenth embodiment of the present invention. FIG. 16 is a fragmentary, top view of the distal portion of the ablation catheter prior to deployment of the conductive hydrogel. In this figure, an opening 160 is present at the extreme distal end 162 of the distal portion $10^X$ of the ablation catheter, and the conductive hydrogel remains within the catheter shaft, behind a shaped, containment membrane 164. In particular, in FIG. 16, the conductive hydrogel 46 has not yet been forced distally in the catheter shaft to "inflate" or "fill" the shaped, containment membrane 164. Although the opening 160 depicted in FIGS. 16-19 is shown as circular, the opening may have a shape other than circular, if desired. The opening 160 and the containment membrane 164 together comprise the hydrogel deployment feature in the tenth embodiment.

Figure 17:
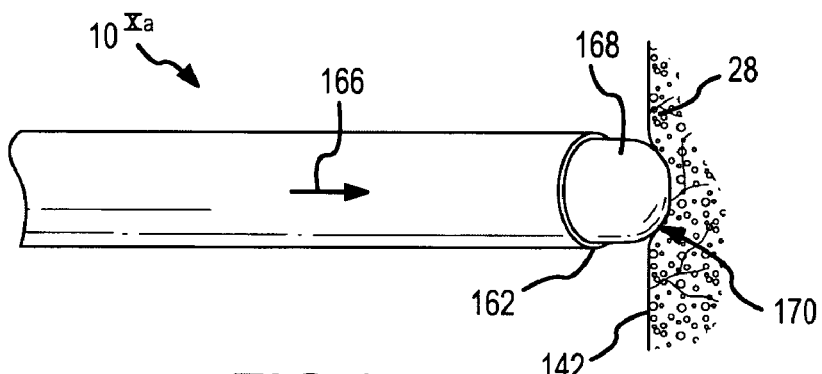
FIGS. 17, 18, and 19 are fragmentary, top views of the distal portion of an ablation catheter according to a first variant, a second variant, and a third variant, respectively, of the tenth embodiment of the present invention.
Figure 18:
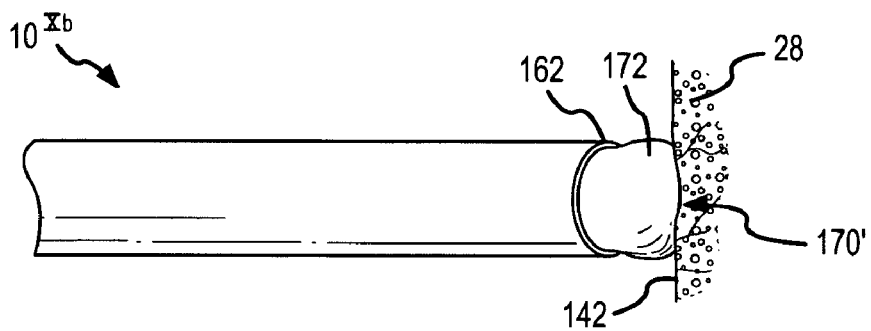
Figure 19:
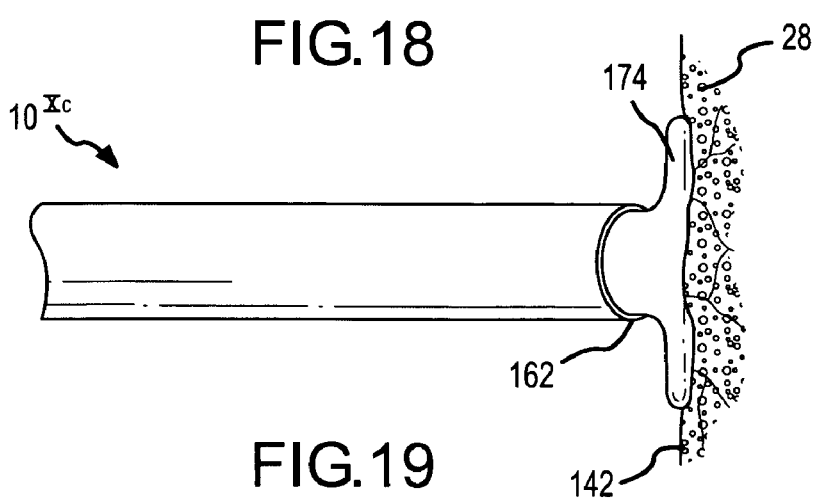

FIGS. 17, 18, and 19 are fragmentary, top views of the distal portion of an ablation catheter according to a first variant $10^{Xa}$, a second variant $10^{Xb}$, and a third variant $10^{Xc}$, respectively, of the tenth embodiment of the present invention. Referring first to FIG. 17, which depicts the first variant $10^{Xa}$ of the tenth embodiment, the conductive hydrogel has been forced longitudinally, distally (i.e., in the direction of arrow 166) within the catheter shaft and has now filled the shaped, containment membrane 168. In this variant, the filled membrane 168 forms a protuberance having a hemispherical configuration. With the conductive hydrogel 46 thus deployed in the containment membrane 168 of this configuration, the distal tip of the ablation catheter may be used to make point or spot ablations 170 or drag burns. In the second variant $10^{Xb}$, which is depicted in FIG. 18, the shaped, containment membrane 172 has a deployed shape that is slightly different from the deployed shape of the containment membrane 168 of FIG. 17. In particular, in the variant $10^{Xb}$ of FIG. 18, the filled containment membrane 172 forms a knoblike protuberance that bulges slightly more adjacent to the surface 142 of the tissue 28 than does the hemispherical protuberance of FIG. 17. Thus, the ablation catheter with the containment membrane 172 of FIG. 18 may be used to make somewhat larger point or spot ablations 170' than the catheter having the containment membrane of 168 FIG. 17.

In FIG. 19, the containment membrane 174 has yet another deployed configuration. In this third variant $10^{Xc}$ of the tenth embodiment of the present invention, the filled containment membrane 174 forms a protuberance at the distal end 162 of the ablation catheter in the shape of a flattened gob that contacts more of the surface 142 of the tissue 28 than is contacted using the membrane shapes 168, 172 respectively depicted in FIGS. 17 and 18. In all of the variants $10^{Xa}$, $10^{Xb}$, $10^{Xc}$ of the tenth embodiment, the protuberance created by the filled containment membrane forms a "conformable surface" that contacts the surface 142 of the tissue 28 to be treated. By adjusting the specific configuration of the shaped, containment membrane, the size and shape of the resulting lesion may be adjusted. The containment membrane also may be hoop-shaped when filled with conductive hydrogel. With such a hoop-shaped or hook-shaped containment membrane, it would be possible to vary the radius of curvature of the resulting, filled, containment membrane by increasing or decreasing the pressure on the hydrogel filling the containment membrane. The ultimate membrane design, configuration, or shape is dictated by the intended ultimate use for the virtual electrode.

FIGS. 20 and 21 depict hydrogel drug delivery catheters. FIG. 20 is a fragmentary, cross-sectional view of the distal portion $176^I$ of a hydrogel drug delivery catheter according to an eleventh embodiment of the present invention; and FIG. 21 is a fragmentary, cross-sectional view of the distal portion $176^{II}$ of a hydrogel drug delivery catheter according to a twelfth embodiment of the present invention. In these embodiments, a "loaded" conductive hydrogel matrix 178 is depicted in the first lumen 134 at the distal portion of the catheter. In particular, a dispensable drug formulation or other beneficial, chemotherapeutic agent 180 is "loaded into" the hydrogel 178 for delivery to the tissue 28. The dispensable drug or other beneficial agent 180 loaded into the hydrogel 178 may be water soluble and ionic (either positive or negative). For example, ionic botox or ionic paxitaxol may be loaded into the hydrogel 178. The dispensable drug or other beneficial agent may be used for the treatment of, for example, cardiac arrhythmias. These catheters may, for example, deliver drugs directly to an area of the heart that is producing arrhythmias to control or eliminate those arrhythmias. The delivered substance may cause a linear lesion or a spot lesion similar to the lesions that are caused by the ablative energy (e.g., RF energy) in the embodiments depicted in FIGS. 1-19.

In the hydrogel drug delivery catheters of FIGS. 20 and 21, the hydrogel deployment feature comprises a permeable or semi-permeable membrane 88 to contain the loaded conductive hydrogel matrix 178 and to thereby minimize the amount of hydrogel 178 potentially entering the patient's bloodstream. Although this membrane is not required, when the membrane is present, the dispensable drug or other beneficial agent 180 permeates the membrane, whereas the hydrogel 178 remains substantially (if not completely) contained inside of the membrane 88.

The embodiment $176^I$ of FIG. 20 is similar to the embodiment $10^{VII}$ of FIGS. 10-14. During use of the catheter depicted in FIG. 20, however, loaded hydrogel 178 is used and a different type of energy is delivered to that hydrogel via the electrode than is delivered during use of the embodiment of FIGS. 10-14. Rather than delivering, for example, RF energy to the tissue 28 (see ablative energy lines 148 in FIG. 14), direct current emanating from the electrode is delivered to the tissue. This embodiment thereby actively delivers the ionic chemotherapeutic substance 180 to the tissue 28. The low-intensity direct current may be used to drive the ionic agent into the tissue by, for example, iontophoresis. FIG. 21 is similar to FIG. 20, but in the twelfth embodiment $176^{II}$ the hydrogel deployment feature comprises a hydrogel slot 158 and membrane 88, similar to what is depicted in the ninth embodiment of FIG. 15.

FIGS. 22-24 depict multi-purpose, multi-electrode hydrogel diagnostic catheters. FIG. 22 is a fragmentary, top view of the distal portion $182^I$ of a diagnostic catheter according to a thirteenth embodiment of the present invention. The distal portion $182^I$ comprises a plurality (e.g., 2 to 50) of isolated, conductive hydrogel disks 184 (or "electrodes") separated by nonconductive hydrogel disks 186. The conductive hydrogel disks 184 and the nonconductive hydrogel disks 186 are adhered together to form the "stack" depicted in, for example, FIG. 22.

FIG. 23 is a fragmentary, cross-sectional view taken along line 23-23 of FIG. 22. FIG. 23 clearly shows that at least one conductive lead 188 is operatively/electrically connected with each conductive hydrogel disk 184. These conductive leads 188, which may be, for example, silver or silver-chloride coated wires, transmit electrical signals to and from the conductive hydrogel disks 184. In this manner, the conductive hydrogel disks may be connected to monitoring equipment outside of the patient, and the catheters depicted in FIGS. 22-24 may be used as diagnostic devices to map the endocardial tissue of the heart at various locations.

FIG. 24 is a fragmentary, end view (looking distally) of the distal portion $182^{II}$ of a diagnostic catheter according to a fourteenth embodiment of the present invention. In this embodiment, the distal portion of the catheter comprises a curved or C-shaped section 190, and the stacked conductive hydrogel disks 184' and nonconductive hydrogel disks 186' are present along an active region of the curved section 190 of the distal portion $182^{II}$ of the diagnostic catheter. The distal portion of the catheter need not be C-shaped and may be formed into any desired shape and configured to any desired size required for a particular application.

The hydrogel diagnostic catheters depicted in FIGS. 22-24 may include shape memory wires or steering wires like those depicted in, for example, FIGS. 12-14 to permit a physician to guide and shape the distal portion of the catheter.

As previously mentioned, the hydrogel used to form the conductive and nonconductive hydrogel disks depicted in the embodiments of FIGS. 22-24 is substantially unaffected by moisture. Therefore, these diagnostic catheters can be placed in, for example, the heart for long periods of time without changing shape. Also, the hydrogel matrix is hydrophilic and, therefore, lubricious, making it easy to move through the patient's vasculature.

Although several embodiments of this invention have been described above with a certain degree of particularity, those skilled in the art could make numerous alterations to the disclosed embodiments without departing from the spirit or scope of this invention. For example, although each of the treatment and diagnostic catheters is depicted in the figures with a circular transverse cross section, the present invention does not require this circular cross section. An important feature in this invention is that hydrogel is used to treat or diagnose tissue. The conductive hydrogel used in the different embodiments described above comprises a desired hydrogel matrix, whether commercially available or specially designed, and includes additives that result in desired electrical and/or chemical properties. For example, the hydrogel matrix may be adjusted to achieve a desired electrical resistance for the conductive hydrogel to minimize, if desired, heating of the hydrogel itself during ablation. In other words, the hydrogel matrix may be adjusted so that most of the ablative energy is delivered to the tissue rather than merely heating up the conductive hydrogel itself. Further, although the devices depicted and described are all uni-polar and, thus, a dispersive electrode (e.g., a grounding pad) may be placed on the patient during use of these devices, certain bi-polar devices that use hydrogel virtual electrodes may also fall within the scope of the present invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of treating cardiac tissue, the method comprising the steps of
    filling at least a distal portion of a catheter lumen of a catheter with conductive hydrogel, said catheter lumen extending adjacent to a catheter active region on a catheter outer surface;
    guiding said catheter active region into contact with the cardiac tissue to be treated;
    activating a hydrogel displacement device to advance said conductive hydrogel toward said active region until said conductive hydrogel broaches said catheter outer surface to thereby introduce at least one conductive hydrogel virtual electrode against the cardiac tissue;
    directing ablative energy through said at least one conductive hydrogel virtual electrode and into the cardiac tissue; and
    activating said hydrogel displacement device to retract said conductive hydrogel and thus said at least one conductive hydrogel virtual electrode from contact with the cardiac tissue and back into said catheter lumen.

2. The method of claim 1, wherein said activating steps further comprise activating a pump to move said conductive hydrogel distally and proximally within said catheter lumen.

3. The method of claim 1, wherein the conductive hydrogel is selected from the group consisting of viscoelastic hydrogel, hemocompatible hydrogel, and radiopaque hydrogel.

4. The method of claim 1,
    wherein a distal portion of the catheter comprises a straight section; a hoop-shaped section; an active region along the hoop-shaped section; and a hydrogel delivery feature along the active region; and
    further comprising orienting the hydrogel delivery feature toward the tissue to be treated.

5. The method of claim 4,
    wherein the hoop-shaped section defines a distally facing surface, wherein the hydrogel delivery feature is on the distally-facing surface, and wherein the hydrogel delivery feature comprises an opening selected from the group consisting of a single row of hydrogel portholes, a plurality of rows of hydrogel portholes, a single hydrogel slot, and a plurality of hydrogel slots; and
    wherein directing ablative energy comprises directing ablative energy through the at least one conductive hydrogel virtual electrode via the hydrogel delivery feature.

6. The method of claim 4,
    wherein the hoop-shaped section defines a distally facing surface, wherein the hydrogel delivery feature is on the distally-facing surface, wherein the distally-facing surface defines a distally facing radial apex, and wherein the hydrogel delivery feature is symmetrically located about the distally facing radial apex; and
    wherein directing ablative energy comprises directing ablative energy through the at least one conductive hydrogel virtual electrode via the hydrogel delivery feature.

7. The method of claim 6,
    wherein the hydrogel delivery feature comprises a plurality of distally-facing hydrogel portholes arranged in a single row along a porthole centerline, and wherein the distally-facing radial apex defines a C shaped line coincident with the porthole centerline; and
    wherein directing ablative energy comprises directing ablative energy through the at least one conductive hydrogel virtual electrode via the plurality of distally-facing hydrogel portholes.

8. The method of claim 6,
    wherein the distally-facing radial apex defines a C shaped line, and wherein the hydrogel delivery feature comprises concentric arcs of hydrogel portholes including a first plurality of hydrogel portholes along an outer arc and a second plurality of hydrogel portholes along an inner arc; and
    wherein directing ablative energy comprises directing ablative energy through the at least one conductive hydrogel virtual electrode via the concentric arcs of hydrogel portholes.

9. The method of claim 8,
    wherein the hydrogel portholes of the first plurality of hydrogel portholes along the outer arc are staggered across the C shaped line from corresponding hydrogel portholes of the second plurality of hydrogel portholes along the inner arc, the first plurality and the second plurality of hydrogel portholes together forming a zigzagging row of hydrogel portholes; and
    wherein directing ablative energy comprises directing ablative energy through the at least one conductive hydrogel virtual electrode via the zigzagging row of hydrogel portholes.

10. The method of claim 6,
    wherein the hydrogel delivery feature comprises a longitudinally-extending hydrogel slot that straddles a slot centerline, and wherein the distally facing radial apex defines a C shaped line coincident with the slot centerline; and
    wherein directing ablative energy comprises directing ablative energy through the at least one conductive hydrogel virtual electrode via the longitudinally-extending hydrogel slot.

11. The method of claim 6,
    wherein the hydrogel delivery feature comprises a plurality of transversely-extending hydrogel slots spaced along a slot centerline, and wherein the distally-facing radial apex defines a C shaped line coincident with the slot centerline; and
    wherein directing ablative energy comprises directing ablative energy through the at least one conductive hydrogel virtual electrode via the plurality of transversely-extending hydrogel slots.

12. The method of claim 4,
    wherein the hoop-shaped section defines a radially outer peripheral wall, wherein the outer peripheral wall defines an outwardly-facing surface, wherein the hydrogel delivery feature is on the outwardly-facing surface, wherein the hydrogel delivery feature comprises at least one opening extending through the outer peripheral wall and the outwardly-facing surface, wherein the at least one opening extends through the outer peripheral wall radially relative to a center of an imaginary circle tracing the hoop shaped section, and wherein the at least one opening is selected from the group consisting of a single row of hydrogel portholes, a plurality of rows of hydrogel portholes radially, a single hydrogel slot, and a plurality of hydrogel slots; and wherein directing ablative energy comprises directing ablative energy through the at least one conductive hydrogel virtual electrode via the hydro gel delivery feature.

13. The method of claim 4,
wherein the hoop-shaped section defines a radially outer peripheral wall, wherein the outer peripheral wall defines an outwardly-facing surface, wherein the hydrogel delivery feature is on the outwardly-facing surface, wherein the outwardly-facing surface defines an outwardly-facing radial apex, and wherein the hydrogel delivery feature is symmetrically located about the outwardly-facing radial apex; and
wherein directing ablative energy comprises directing ablative energy through the at least one conductive hydrogel virtual electrode via the hydrogel delivery feature.

14. The method of claim 13,
wherein the hydrogel delivery feature comprises a plurality of outwardly-facing hydrogel portholes arranged in a single row along a porthole centerline, and wherein the outwardly-facing radial apex defines a C shaped line coincident with the porthole centerline; and
wherein directing ablative energy comprises directing ablative energy through the at least one conductive hydrogel virtual electrode via the plurality of outwardly-facing hydrogel portholes.

15. The method of claim 13,
wherein the outwardly-facing radial apex defines a C shaped line, and wherein the hydrogel delivery feature comprises side by side arcs of hydrogel portholes including a first plurality of hydrogel portholes along a distal arc and a second plurality of hydrogel portholes along a proximal arc; and
wherein directing ablative energy comprises directing ablative energy through the at least one conductive hydrogel virtual electrode via the first plurality and the second plurality of hydrogel portholes.

16. The method of claim 13,
wherein the hydrogel delivery feature comprises a longitudinally-extending hydrogel slot that straddles a slot centerline, and wherein the outwardly-facing radial apex defines a C shaped line coincident with the slot centerline; and
wherein directing ablative energy comprises directing ablative energy through the at least one conductive hydrogel virtual electrode via the longitudinal-extending hydrogel slot.

17. The method of claim 1,
wherein a distal portion of the catheter comprises a straight active region, the straight active region extending parallel to a catheter longitudinal axis; and a hydrogel delivery feature along the straight active region; and further comprising orienting the hydrogel delivery feature toward the tissue to be treated.

18. The method of claim 1,
wherein the catheter comprises a first lumen adapted to contain a displaceable segment of the conductive hydrogel used to form the at least one hydrogel virtual electrode; and
wherein activating the hydrogel displacement device comprises moving the displaceable segment of the conductive hydrogel.

19. The method of claim 18,
wherein the first lumen comprises a nearly circular subportion and a rounded-rectangular subportion, and wherein the rounded-rectangular subportion retains an electrode adapted to deliver ablative energy through the at least one conductive hydrogel virtual electrode to the tissue being treated; and
wherein directing ablative energy comprises directing ablative energy via the electrode in the rounded-rectangular subportion.

20. The method of claim 18,
wherein the catheter further comprises a second lumen adapted to contain a steering wire; and
further comprising manipulating the steering wire to position the at least one conductive hydrogel virtual electrode against the tissue being treated.

21. The method of claim 1,
wherein the at least one conductive hydrogel virtual electrode is contained within a containment membrane; and
further comprising contacting the tissue to be treated with the containment membrane.

22. The method of claim 21, wherein the membrane is selected from the group consisting of permeable and semipermeable membranes.

23. The method of claim 21,
wherein the membrane comprises a shaped membrane; and
further comprising filling the shaped membrane with conductive hydrogel to produce a predetermined configuration.

24. The method of claim 23,
wherein the catheter has a distal portion comprising a hydrogel delivery feature which includes an opening adapted to be placed adjacent to the tissue to be treated and the containment membrane; wherein the containment membrane is secured at the opening; and
further comprising filling the containment membrane with conductive hydrogel to form a protuberance having a conformable surface to contact the tissue to be treated.

25. The method of claim 24, wherein the protuberance is selected from the group consisting of a hemisphere, a knob, a flattened gob, a hook, and a hoop.

* * * * *